United States Patent [19]

Cook

[11] Patent Number: 5,989,854
[45] Date of Patent: *Nov. 23, 1999

[54] VESSELS AND MULTIWELL PLATES HAVING A SCINTILLANT BASE

[75] Inventor: Neil David Cook, Beaconsfield, United Kingdom

[73] Assignee: Amersham International plc, United Kingdom

[ * ] Notice: This patent is subject to a terminal disclaimer.

[21] Appl. No.: 08/742,497

[22] Filed: Nov. 1, 1996

Related U.S. Application Data

[63] Continuation-in-part of application No. 08/373,316, filed as application No. PCT/GB94/01040, May 16, 1994, Pat. No. 5,665,562.

[30] Foreign Application Priority Data

May 17, 1993 [EP] European Pat. Off. .............. 93303806

[51] Int. Cl.⁶ ...................................................... C12Q 1/16
[52] U.S. Cl. ................................ 435/35; 422/71; 436/804
[58] Field of Search ................................. 435/4, 7.1, 7.2, 435/29, 35; 436/57, 531, 535, 537, 804, 805; 422/71

[56] References Cited

U.S. PATENT DOCUMENTS

| | | | |
|---|---|---|---|
| 5,496,502 | 3/1996 | Thomson | 252/301.17 |
| 5,665,562 | 9/1997 | Cook | 435/35 |

FOREIGN PATENT DOCUMENTS

| | | |
|---|---|---|
| 0 576 090 | 12/1993 | European Pat. Off. . |
| WO 90/03844 | 4/1990 | WIPO . |

OTHER PUBLICATIONS

Amersham Life Science, *Proximity News*, Issue No. C1 (Apr. 1996).

*Primary Examiner*—Ralph Gitomer
*Attorney, Agent, or Firm*—Wenderoth, Lind & Ponack, L.L.P.

[57] ABSTRACT

A vessel, or an array of vessels, in the form of a multiwell plate, wherein the side walls are opaque and non-scintillant, and wherein the base comprises a scintillant substance, said base being formed of a plastics material which does not permit the attachment or growth of cells.

10 Claims, 6 Drawing Sheets

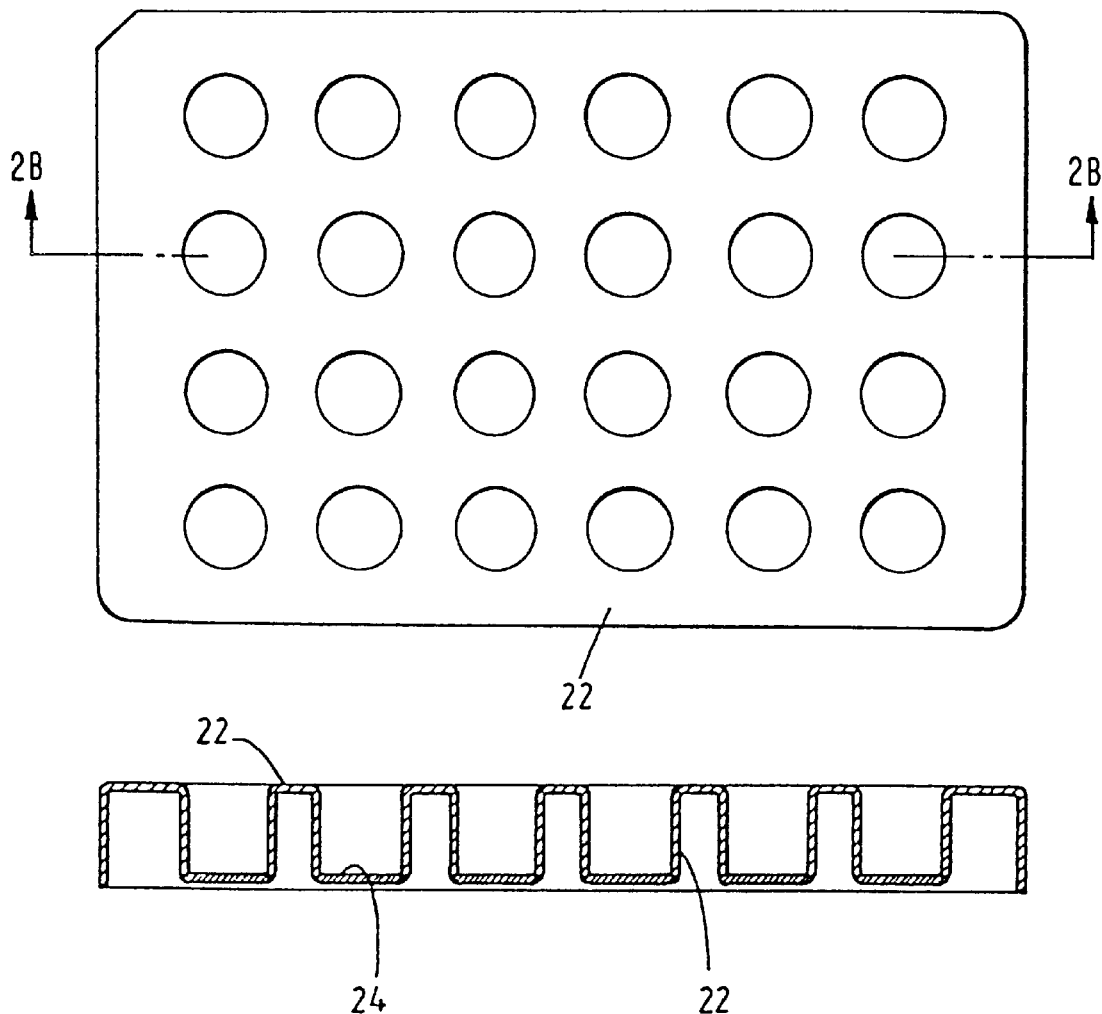

Binding of Radiolabelled SLex-Glycoconjugate to E-selectin coated Scintillation Microtitre Plates Standard Curve for the Radioimmunoassay of ET-1 using Anti-ET-1(15-21) Rabbit IgG Coated Scintillation Microtitre Plates

VESSELS AND MULTIWELL PLATES HAVING A SCINTILLANT BASE

This application is a continuation-in-part of Ser. No. 08/373,316, filed Jan. 17, 1995 which is a 371 of PCT/GB94/01040 filed May 16, 1994, now U.S. Pat. No. 5,665,562 issued Sep. 9, 1997.

FIELD OF THE INVENTION

The present invention relates to the study of cellular and biochemical processes in living cells or in components of cells. Specifically described are devices and methods for the study of cellular and biochemical processes, utilizing the Scintillation Proximity principle.

BACKGROUND OF THE INVENTION

1. Studies of Cellular Processes in Living Cells

Mammalian cell culture is an essential tool for fundamental research in eukaryotic biology and it has contributed to advances in virology, somatic cell genetics, endocrinology, carcinogenesis, toxicology, pharmacology, immunology and developmental biology (McKeehan, W. I., *In Vitro Cell Dev. Biol.*, 26, 9–23, (1990)). Classical cell culture technology is carried out in nutrient mixtures with cells usually cultured as a monolayer attached to a hydrophilic surface, commonly sterile treated polystyrene. Considerable progress has been made in developing cell culture systems for specific cell types, with the aim of reconstructing the cell and its environment into a defined unit for the study of responses and properties of cells in a dynamic context. However, experimentation on such culture systems using biological assays is often limited by the need to use invasive or disruptive processes that compromise the structural and functional integrity of the cells.

Certain types of investigations lend themselves particularly to studies with whole cells and inevitably require cell culture techniques as an essential step in the investigation. General areas of study include:

(i) intracellular activity, including the replication and transcription of nucleic acids, protein synthesis and lipid metabolism, (ii) intracellular flux, i.e. movement of RNA from cell nuclei to the cytoplasm, translocation of human receptor complexes, fluctuations in lipid and protein metabolic pools, transport of ions and other small molecules across membranes, (iii) environmental influences, including nutrition, infection, virally or chemically induced transformation, drug action and metabolism, response to external stimuli and secretion of specialized products, and (iv) cell-cell interaction, including embryonic induction, cell population kinetics, cell-cell adhesion and motility.

A vast array of radiolabelled ligands which are available commercially, has played a major role in the development of methods currently used to study intracellular activity, metabolism and cell-ligand interactions in cell culture assay systems. Particular examples relating to the study of cellular processes are:

Thymidine Uptake

Studies involving the measurement of [$^3$H]thymidine uptake currently suffer from an absolute requirement for cell disruption and consequently are prone to artifactual effects (Adams, R. L. P., *Cell Culture for Biochemists*, p 181–192; Saegusa, Y. et al, *J. Cell Physiol.*, 142, 488–495 (1990)). In addition to providing an assessment of cellular proliferation and growth in living cells, thymidine uptake studies are also used to study the extent of DNA repair and/or damage occurring during culture, in the presence or absence of external agents (McKeehan, W. et al, *In Vitro Cell Dev. Biol.*, 26, 9–23, (1990)). Current methods however, require cell disruption and do not readily lend themselves to temporal studies. Thymidine uptake has been used more recently, in tandem with other potential markers, in the field of programmed cell death, or apoptosis, where there is currently considerable pharmacological and clinical interest (Tritton, T. and Hickman, J., *Cancer Cells Quarterly Rev.*, 2, 95–105, (1990)). However, few of the current methods are able to explore and quantify spatial and temporal events occurring during apoptosis (Lock, R. B. and Ross, W. E., *Proc. Amer. Assoc. Cancer Res.*, 30, 621, (1989)). [$^3$H]Thymidine uptake studies are also used in cell cycle studies in order to monitor regulation of this essential process (Studzinski, G. P., *Cell Tissue Kinetics*, 22, 405–424, (1989)). However, there are currently no methods available for the direct measurement of thymidine uptake in living cells.

Receptor Binding/Kinetic Studies

Most of the methods used in this field require binding of a radiolabelled ligand, followed by quantification of receptor number and affinity in competition studies at a fixed time (Goldstein, J. L. and Brown, M. S., *Methods in Enzymol.*, 98, 241–260, (1985); Zoon, K. C. et al, *J. Pharmaceutical and Biochemical Analysis*, 7, 147–154, (1989)). These methods often utilize membrane filter assays in vitro. The majority of methods require release of cells from a monolayer and often necessitate isolation of cell membranes. These systems are therefore not suitable for real time kinetic studies. Thus in the cytokine field, where specific ligand-receptor binding studies are of fundamental importance, it is not possible to monitor binding, uptake and internalization of specific radiolabelled ligands, as a function of time in living cells (Rakowicz-Szulczynska, E. W., et al, *J. Immunol. Methods*, 116, 167–173, (1989)). Currently disruptive techniques are required to differentiate between these important processes. This is also the case for studies of receptor cycling, an important process during the receptor-mediated endocytosis of a variety of essential ligands (Anderson, R. G. W., et al, *Cell*, 10, 351–364, (1977)).

Lipid Metabolism

Studies on the regulation of lipid biosynthesis are usually limited by the disruptive experimental procedures required to determine the incorporation of radioactively labeled lipid substrates. Such experiments are generally performed under optimal conditions in vitro, that may not reflect the situation in vivo, due to an inability to measure variations, both temporally and spatially, in living cells (Vance, D. E. and Vance, J. E., *Biochemistry of Lipids and Membranes*, pp.116–120, (1989)). The Hep G2 human tumorigenic cell line is currently widely used to investigate lipid and lipoprotein metabolism. Pulse-chase studies are currently difficult to perform when using radiolabelled precursors such as oleic acid, as a function of time. This is because there is a requirement for disruption of the cell in order to differentiate localized areas of uptake. To date, the only metabolic studies that can be carried out with living cells have used fluorescently labeled lipids (Pownall, H. J., *Chem. Physics of Lipids*, 50, 191–212, (1989)). There are, however, inherent problems with such studies since the fluorophors used tend to be extremely bulky relative to the lipid. The physiological integrity of such labeled lipids is therefore questionable and they are known to be taken up in Hep G2 cells at different rates and incorporated differently within the cell, relative to unlabelled lipid (Pownall, H. J.). Similar problems are also encountered in studies related to protein uptake and metabolism as seen for example when pulse-chase studies using radiolabelled methionine and/or leucine are carried out (Freshney, R. I., *Culture of Animal Cells: A Manual of Basic Technique*, 2nd Edition, Alan R. Liss Inc. (1987), pages 227–236). Unless fluorescent probes are used, disruption of the cell is always necessary (Smith, L. C., et al, *Methods in Enzymol.*, 129, 858–873, (1986)).

Cell Calcium

Calcium concentrations in the cytoplasm are carefully regulated by several mechanisms and the affinity for calcium and its rate of transport across the membrane, vary considerably from cell to cell. In early cellular studies, calcium sensitive fluorescent dyes were injected invasively, thus restricting their usefulness in kinetic measurements. The more recent use of dyes such as Fura-2 has alleviated this problem, although quantitative, time-dependent measurements of calcium are still difficult to carry out in culture (Cavaggioni, A., *Bioscience Results,* 9(4), 421, (1989)). Alternatively, [$^{45}$Ca] (Kuwata, J. H. and Langer, G. A., *Molecular Cell Cardiology,* 21, 1195–1208, (1989)) and Langer, G. A. et al., *Circulation Res.,* 24, 589–597, (1969)) and $^{42}$K (Frank, J. S. et al, *Circulation Res.,* 41, 702–714, (1977)) exchange has been measured in cardiac cells. Using sterile scintillant coated discs in a flow cell chamber, neonatal rat hearts were cultured and the time dependent uptake of [$^{45}$Ca] and [42 K] was monitored by pulse-chase methods. Although time dependent measurements in living cells are recorded in this study, there are several disadvantages with this system: (i) the system is only applicable to one sample at a time, (ii) large quantities of [$^{45}$Ca] are used for uptake studies, (iii) there is a high background/non-specific signal and (iv) discs are removed from the sterile culture medium and exposed to air before insertion into the flow cell. There is therefore no opportunity to perform additional measurements or to continue to culture the sample.

Consequently, there is still a requirement, not only in this case for calcium uptake measurement, but also in the processes described previously, for non-invasive, non-disruptive, real-time whole cell measurements in a format which is amenable to high sample throughput. The invention described here is intended to overcome the problems and limitations of the prior art methods and will greatly facilitate the above objectives.

2. Developments in Scintillation Counting Technology

Detection of receptor binding or cellular metabolic events utilizing radiolabelled substrates is accomplished by scintillation counting, usually following extraction or separative procedures, which are generally laborious, time consuming and are not amenable to automation.

A means for overcoming such problems is described in U.S. Pat. No. 4,568,649 (Bertoglio-Matte). This covers an homogeneous assay procedure which produces quantifiable light energy at a level which is related to the amount of radioactively labeled reactant in the assay medium. The light energy is produced by a scintillant which is either incorporated, or forms part of, a support structure (beads or other solid surface which can be used in the assay process). The support structures are coated with a receptor or other capture molecule, and are therefore capable of specifically binding the radiolabelled ligand or reactant of interest. In a direct assay, a sample containing the reactant is mixed in aqueous solution containing scintillant support bodies to which a binding compound may be attached. The reactant is caused to bind with its corresponding binding compound, thereby placing the radiolabelled species in close proximity to the scintillant-containing support. The scintillant is activated causing emission of light, which can be detected conventionally using a scintillation counter. The amount of light produced is directly proportional to the amount of reactant bound to the surface of the support structures.

Ideally the isotope of the radiolabel should have a relatively low energy beta-emission, for example tritium, or iodine-125 auger electrons. Only that portion of the sample which binds to the binding molecule, and is therefore in close proximity to the scintillant will result in scintillation events that can be counted. Unbound reactant will be at too great a distance from the scintillant surface to produce scintillations, the beta-decay energy being dissipated in the liquid aqueous medium.

A considerable advantage of the scintillation proximity assay process is that it does not require separation of bound molecular species from free. Such a process will also minimize the need to handle potentially hazardous/radioactive substances, as well as being more convenient and amenable to automation.

In U.S. Pat. No. 4,568,649, capture molecules are attached to, and fluorescer is integrated into beads, for example polyacrylamide beads. The Scintillation Proximity Assay technique may also be performed with other types of support structure. European Patent Application No. 0378059 describes a support structure for scintillation proximity assays comprising a fibre mat which incorporates a fluorescer. In one format the fibre mat consists of solid scintillant forming a matrix. The scintillant can be a cerium loaded glass or may be based in rare earths such as yttrium silicate (with or without activators such as $Tb^{3+}$, $Eu^{3+}$, $Li^+$). The scintillant fibre may also be composed of a scintillant polymer such as polyvinyltoluene. As an alternative, an organic scintillant such as 2,5-diphenyloxazole (PPO) or anthracene may be coated onto a fibre mat which is made from non-scintillant material. The fibre mesh format presents a large surface area upon which binding reactions can occur.

PCT Application No. WO 90/03844 discloses a microtitre well plate intended for binding assays. There is no claimed application for living cell-based assays. The sample plate may be produced from a transparent scintillant-containing plastic by means of a vacuum thermoforming or injection moulding process. In principle the walls of the plate may be coated with binding compound for the purpose of carrying out in vitro binding assays using radiolabelled reactants. However no practical examples are given in the application. It is possible, for example, that one disadvantageous effect of using a plate made from clear plastic will be that light generated in one well of the plate may be detected in adjacent wells, a phenomenon known as "cross talk", thereby causing high assay backgrounds and spurious assay results. The plates are not described as being treated in any way to support cell culture or growth.

Burton, J. A. and Hoop, B. describe a method and apparatus for ligand detection (PCT Application No. WO 88/04429). Central to the process is a reaction chamber and sensor surface connected optically to a detector. In a typical format of the method, a sample containing the ligand to be measured is introduced into the chamber containing receptor molecules immobilized on the sensor surface, and radioactively labeled ligand molecules. As a result, a portion of the labeled ligand molecules is displaced from the surface causing a decrease in fluorescent events at the sensor surface. However, the apparatus described in this application is designed for continuous throughput competitive binding assays. There is no reference to, or applications in, the study of living cells.

In summary, none of the prior art methods published for SPA are amenable to the study of biochemical processes in living cells. In part, this is due to the fact that the current fibre and bead based technologies are not suitable for monolayer cell culture. The only scintillant plate format so far described is intended for in vitro radiolabelled binding assays, and furthermore has inherent potential disadvantages outlined above for the specific applications which are the subject of this invention.

DESCRIPTION OF THE INVENTION

This invention provides in one aspect apparatus for studying a cellular process, comprising a vessel having an axis, an open top, side walls and a base, wherein the base includes a region and there is provided in or on an interior surface of the region a layer comprising a scintillant substance and being adapted for the attachment and/or growth of cells.

In one embodiment, the layer comprising a scintillant substance constitutes a base plate integral with the base of the vessel. In another embodiment, the layer comprising a scintillant substance is a disc positioned on the base of the vessel.

The invention also provides in another aspect a multiwell plate, such as a microtitre plate, comprising an array of wells held in fixed relationship to one another, wherein each well is a vessel as defined.

The invention provides in another aspect a method of studying a cellular process, by the use of a vessel as defined and of detection means for observing scintillation of the scintillant material, which method comprises providing cells adhering to the layer in the presence of a fluid medium, introducing into the fluid medium a reagent labeled with a radioisotope emitting electrons with a mean range up to 2000 μm, preferably up to 200 μm, in aqueous media, under conditions to cause a portion of the labeled reagent to become associated with or released from the cells adhering to the layer, and using the detection means to observe scintillation caused by radioactive decay so as to study the cellular process.

The invention provides in another aspect a method of studying a cellular process, by the use of a vessel as defined, and of detection means for observing scintillation of the scintillant substance, which method comprises introducing into the vessel a fluid suspension of cells or other structures labeled with a radioisotope emitting electrons with a mean range of up to 2000 μm in aqueous media, under conditions to cause a portion of the labeled cells or other structures to become associated with the layer, and using the detection means to observe scintillation caused by radioactive decay so as to study the cellular process.

The apparatus and method can be used for the measurement of a variety of cellular biochemical processes in real time using non-invasive techniques, that is to say techniques which do not compromise the integrity or viability of the cells.

The apparatus can also be used in a method for performing radiolabelled binding assays, to determine the presence or concentration of a reactant of interest, using the vessel or the multiwell plate defined above and detection means for observing scintillations of the scintillant material. The method comprises providing a binding component which is coated onto the surface of the well. The binding component may be capable of reacting specifically with the reactant of interest. Upon introducing into the sample well a radiolabelled reactant, the radiolabelled reactant binds to the binding component to an extent related to the presence or the concentration of the reactant of interest. The radiation emitted by the bound reactant is close enough to the scintillant base of the well to cause light emissions which may be detected by detection means for observing scintillation events. Any unbound radiolabelled reactant is generally too far away from the surface of the scintillant base of the well, the radiation energy being dissipated into the aqueous environment and the radioactive disintegrations will remain undetected by the detector.

The apparatus can also be used in a method for determining enzyme activities using the vessel or the multiwell plate and detection means for observing scintillations of the scintillant material. The method comprises providing an enzyme substrate which is bound onto the surface of the well, introducing into the sample well the enzyme under study and a radiolabelled reactant, such that an enzyme-mediated reaction occurs with the formation of radiolabelled product. The radioactive emissions emitted by the bound labeled product are close enough to the scintillant base of the well to cause light emissions which may be detected by the detection means for observing scintillation events. Unbound radiolabelled reactant is generally too far away from the surface of the scintillant base of the well, the radiation energy being dissipated into the aqueous environment and the radioactive disintegrations will remain undetected by the detector.

In an alternative format, the bound enzyme substrate is labeled and the enzyme causes cleavage of a labeled portion of the substrate. In this format, the scintillation events decrease as a result of the removal of the radiolabel from the bound substrate.

Thus, the apparatus of the present invention may be used for in vitro measurements in a variety of assay types, utilizing a binding component or an enzyme substrate which is coated either directly or indirectly onto the surface of the scintillant base of the well, and a reactant, which may be labeled with a suitable radioisotope. A binding component is a substance which, when bound to the surface of the well, is capable of binding a specific reactant, thereby bringing the reactant into close proximity with the well surface. Examples of binding component-reactant pairs include: (strept)avidin-biotin, antibody-antigen, DNA-DNA, DNA binding protein-DNA, DNA-RNA, polysaccharide-lectin. Such assays which may be performed according to this invention include: direct or competitive binding assays, for example radio-immunoassays, radio-receptor binding assays, DNA-DNA probe binding assays, DNA-RNA binding assays, enzyme assays and the like.

Application of the method is not restricted to any particular analytes, class of substances, or binding component-reactant pair and in principle any binding assay may be performed according to the invention. Likewise, the assay format may be one of any of the generally recognized types, including, i) signal addition, in which a radiolabelled donor is added to an inactive substrate bound to the surface of the well, ii) signal removal, in which a radiolabelled substrate, already linked to the well surface, is removed generally by the action of an enzyme, and iii) product capture, in which the radiolabelled reactant, optionally in the presence of unlabelled sample reactant, is bound to the binding component, by means of a specific interaction between the reactant and the binding component linked to the surface of the well.

The scintillant base plate is preferably optically transparent, both to allow cells in culture to be viewed using an inverted phase contrast microscope, and to enable the material to transmit light at a given wavelength with maximum efficiency. In addition the base retains its optical properties even after exposure to incident beta radiation from radioisotopes as well as under stringent radiation conditions required for sterilization of the plates.

The base plate can be composed of any transparent material containing scintillant, e.g. a scintillant glass based on lanthanide metal compounds. In the preferred format, the base plate is composed of any plastic material, where normally the monomer units which comprise the polymer include phenyl or naphthyl moieties, in order to absorb incident radiation energy from radionuclides which are in close proximity with the surface. Preferably the plastic base plate is composed of polystyrene or polyvinyltoluene, into which is incorporated a scintillant substance. The scintillant substance can include aromatic hydrocarbons such as p-terphenyl, p-quaterphenyl and their derivatives, as well as derivatives of the oxazoles and 1,3,4-oxadiazoles, such as 2-(4-t-butylphenyl)-5-(4-biphenylyl)-1,3,4-oxadiazole and 2,5-diphenyloxazole. Also included in the polymeric composition may be a wavelength shifter such as 1,4-bis(5-pheny-2-oxazolyl)benzene, 9,10-diphenylanthracene, 1,4-bis(2-methylstyryl)-benzene etc. The function of the wavelength shifter is to absorb the light emitted by the scintillant substance and re-emit longer wavelength light which is a better match to the photo-sensitive detectors used in scintillation counters. Other scintillant substances and polymer bodies containing them are described in EPA 556005. The nature of the scintillant substance is not material to the invention.

The scintillant substances can be incorporated into the plastic material of the base by a variety of methods. For example, the scintillators may be dissolved into the monomer mix prior to polymerization, so that they are distributed evenly throughout the resultant polymer. Alternatively the scintillant substances may be dissolved in a solution of the polymer and the solvent removed to leave a homogeneous mixture.

The base plate or disc may be bonded to the main body of the well or array of wells, which itself may be composed of a plastic material consisting of polystyrene, polyvinyltoluene, etc. In the case of the multi-well array, the body of the plate may be made opaque, i.e. non-transparent and internally reflective, in order to completely exclude transmission of light and hence minimize "cross-talk". This is accomplished by incorporating into the plastic at the polymerization stage a white dye or pigment, for example, titanium dioxide. Bonding of the base plate to the main body of the device can be accomplished by any suitable bonding technique, for example heat welding, injection moulding or ultrasonic welding.

BRIEF DESCRIPTION OF THE DRAWINGS

Reference is directed to the accompanying drawings, in which:

FIGS. 2A and B are a two-part orthogonal view of another multiwell plate according to the invention;

Referring to FIGS. 1A and B, a 96-well device is constructed to the standard dimensions of 96-well microtitre plates 12.8 cm×8.6 cm×1.45 cm with wells in an array of 8 rows of 12 wells each. The main body of the plate (Part A) is constructed by injection moulding of polystyrene containing a loading of white titanium oxide pigment at 12%. At this stage, the wells 12 of the microtitre plate 10 are cylindrical tubes with no closed end. A base plate (Part B) is formed by injection moulding of polystyrene containing 2-(4-t-butylphenyl)-5-(4-biphenylyl)-1,3,4-oxadiazole (2%) and 9,10-diphenylanthracene (0.5%). The base plate (Part B) has been silk screen printed with a grid array 14 to further reduce crosstalk. The base plate (Part B) is then fused in a separate operation to the body (Part A) by ultrasonic welding, such that the grid array 14 overlies the portions of the microtitre plate 10 between the wells 12.

Referring to FIGS. 2A and B, a 24-well device is constructed to the dimensions 12.8×8.6×1.4 cm with 24 wells in an array of 4 rows of 6 wells. The main body 22 of the plate (not including the base of each well) is constructed by injection moulding of polystyrene containing 12% white titanium oxide pigment. The base 24 of each well is injection moulded with polystyrene containing 2-(4-t-butylphenyl)-5-(4-biphenylyl)-1,3,4-oxadiazole (2%) and 9,10-diphenylanthracene (0.5%). The heat from the injected base plastic results in fusion to the main body giving an optically transparent base to the well.

Figure 1A:
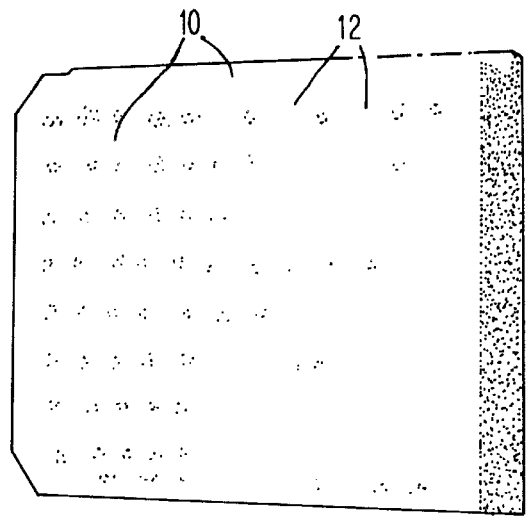
FIGS. 1A and B are a two-part perspective view of a multiwell plate according to the invention.
Figure 1B:
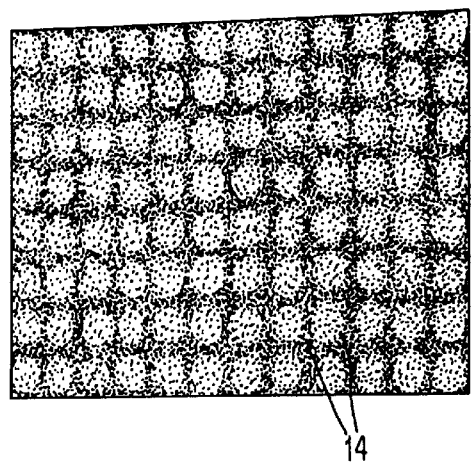

When compared to the microtitre plate shown in FIGS. 1A and B, the design shown in FIGS. 2A and B is fundamentally different in that the base of each well is discontinuous with the other wells in the array. In this embodiment the printed grid (used in FIGS. 1A and B) is not required to reduce inter-well crosstalk. Either construction may be used for 96-well, 24-well or other embodiments of the device.

Figure 3:
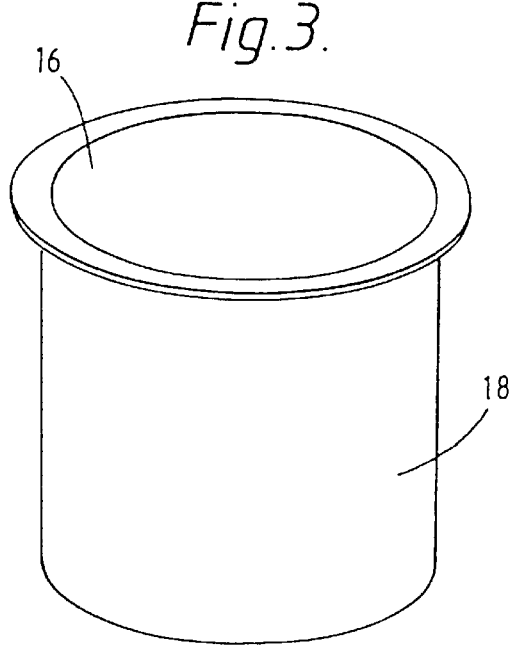
FIG. 3 is a perspective diagrammatic view of a single well device with a scintillant plastic base.

FIG. 3 shows a single vessel according to the invention having an open top 16, side walls 18 and an optically transparent scintillant plastic base 20 sealed round the lower edge of the side walls.

In this invention, the device can take various formats for the purpose of growing cells and studying cellular biochemical processes in living cells or cell fragments. In one format the device consists of a 96-well plate (shown in FIGS. 1A and B), which is a format typically used in experimental cell biology and one which is also suitable for use in a flat bed scintillation counter (e.g. Wallac Microbeta or Packard Top Count). In the multi-well format, it is an advantage to be able to prevent "cross talk" between different wells of the plate which may be used for monitoring different biological processes using different amounts or types of radioisotope. Therefore the main body of the plate is made from opaque plastic material.

As an alternative format (FIGS. 2A and B), the device may be in the form of a 24-well plate which is a more commonly used format for cell culture. This type of plate is also suitable for counting in a flat bed scintillation counter. The dimensions of the wells will be larger enabling more cells to be grown.

In another format (FIG. 3), the invention consists of a single well or tube. The tube may be constructed from a hollow cylinder made from optically transparent plastic material and a circular, scintillant containing, plastic disc. The two components are welded together so as to form a single well or tube suitable for growing cells in culture. As in the plate format, bonding of the circular base plate to the cylindrical portion is achieved by any conventional bonding technique, such as ultrasonic welding. The single well or tube may be any convenient size, suitable for scintillation counting. In use, the single well may either be counted as an insert in a scintillation vial, or alternatively as an insert in a multi-well plate of a flat bed scintillation counter. In this latter case, the main body of the multi-well plate would need to be opaque for reasons given earlier.

As an alternative non-preferred format, the transparent, scintillant containing plastic disc is made to be of suitable dimensions so as to fit into the bottom of a counting vessel. The counting vessel is made from non-scintillant containing material such as glass or plastic and should be sterile in order to allow cells to grow and the corresponding cellular metabolic processes to continue. Cells are first cultured on the disc, which is then transferred to the counting vessel for the purposes of monitoring cellular biochemical processes.

The culture of cells on the scintillation plastic base plate of the wells (or the disc) involves the use of standard cell culture procedures, e.g. cells are cultured in a sterile environment at 37° C. in an incubator containing a humidified 95% air/5% $CO_2$ atmosphere. Various cell culture media may be used including media containing undefined biological fluids such as foetal calf serum, or media which is fully defined and serum-free. For example, MCDB 153 is a selective medium for the culture of human keratinocytes (Tsao, M. C., Walthall, B. J. and Ham, R. G., *J. Cell. Physiol.*, 110, 219–229, (1982)).

The invention is suitable for use with any adherent cell type that can be cultured on standard tissue culture plasticware. This includes the culture of primary cells and both normal and transformed cell-lines. These cells may be derived from all recognized sources with respect to (i) species, e.g. human, rodent, simian, (ii) tissue source, e.g. brain, liver, lung, heart, kidney, skin, muscle and (iii) cell type, e.g. epithelial, endothelial, mesenchymal, neuroectodermal. In addition, cells that have been transfected with recombinant genes may also be cultured using the invention. There are established protocols available for the culture of many of these diverse cell types (Freshney, R. I., *Culture of Animal Cells: A Manual of Basic Technique*, 2nd Edition, Alan R. Liss Inc. (1987)). These protocols may require the use of specialized coatings and selective media to enable cell growth and the expression of specialized cellular functions. However, none of these protocols are precluded from use in the invention.

The scintillating base plate or disc, like all plastic tissue culture ware, requires surface modification in order to be adapted for the attachment and/or growth of cells. Treatment preferably involves the use of high voltage plasma discharge, a well established method for creating a negatively charged plastic surface (Amstein, C. F. and Hartmann, P. A., *J. Clinical Microbiol.*, 2,1, 46–54, (1975)). For many cell types, this surface is suitable for both growth and assay purposes. However, cell attachment, growth and the expression of specialized functions can be further improved by applying a range of additional coatings to the culture surface of the device. These can include: (i) positively or negatively charged chemical coatings such as poly-lysine or other biopolymers (McKeehan, W. L. and Ham, R. G., *J. Cell Biol.*, 71, 727–734, (1976)); (ii) components of the extracellular matrix including collagen, laminin, fibronectin (Kleinman, H. K. et al, *Anal. Biochem.*, 166, 1–13, (1987)) and (iii) naturally secrete extracellular matrix laid down by cells cultured on the plastic surface (Freshney, R. I.). Furthermore, the scintillating base plate may be coated with agents such as lectins, or adhesion molecules to enable the attachment of cell membranes or cell types that normally grow in suspension. Methods for the coating of plasticware with such agents have been described previously, see for example, Boldt, D. T. and Lyons, R. D., *J. Immunol.*, 123, 808, (1979)).

In addition, the surface of the scintillating layer may be coated with living or dead cells, cellular material, or other coatings of biological relevance. The interaction of radiolabelled living cells, or other structures with this layer can be monitored with time allowing processes such as binding, movement to or from or through the layer to be measured.

Virtually all types of biological molecules can be studied using this invention. That is, any molecule or complex of molecules that interact with the cell surface or that can be taken up, transported and metabolized by the cell, can be examined using real time analysis. Examples of biomolecules will include, receptor ligands, protein and lipid metabolite precursors, (e.g. amino acids, fatty acids), nucleosides and any molecule that can be radiolabelled. This would also include ions such as calcium, potassium, sodium and chloride, that are functionally important in cellular homeostasis, and which exist as radioactive isotopes. Furthermore, viruses and bacteria and other cell types, which can be radiolabelled as intact moieties, can be examined for their interaction with monolayer adherent cells grown in the scintillant well format.

The type of radioactive isotope that can be used with this system will typically include any of the group of isotopes which emit electrons having a mean range up to 2000 $\mu$m in aqueous media. These will include isotopes commonly used in biochemistry such as [$^3$H], [$^{125}$I], [$^{14}$C], [$^{35}$S], [$^{45}$Ca], [$^{33}$P] and [$^{32}$P], but does not preclude the use of other isotopes such as [$^{55}$Fe], [$^{109}$Cd] and [$^{51}$Cr] which also emit electrons within this range. The wide utility of the invention for isotopes of different emission energy is due to the fact that the current formats envisaged would allow changes to the thickness of the layer comprising a scintillant substance, thereby ensuring that all the electron energy is absorbed by the scintillant substance. Furthermore, cross-talk correction software is available which can be utilized with all high energy emitters.

The following Examples were performed using a multi-well plate as described with reference to FIGS. 1A and B, in which each well has opaque non-scintillant side walls and a base formed of a polymer containing a scintillant substance.

EXAMPLE 1

MEASUREMENT OF THE ADHESION OF A SLe$^x$ CONTAINING GLYCOCONJUGATE TO IMMOBILIZED E-SELECTIN

Introduction

The emigration of leucocytes from the post-capillary venules into the tissues during an inflammatory response is a multistage process which involves several families of cell adhesion molecules. The first stage, in which leucocytes tether to and roll along the vessel endothelium, is mediated by the interaction of members of the selectin family with their complementary counter-receptors [Springer, T. A., (1994), *Cell*, 76, 301–314]. The selectin family has three structurally related members. E-selectin is expressed on activated endothelium, P-selectin is expressed on activated endothelium and platelets, while L-selectin is expressed on circulating leucocytes [Tedder, T. F., et al., (1995), *FASEB*, 9, 866–873].

The selectins recognize carbohydrate ligands presented by a number of recently identified glycoproteins. It is believed that the minimal carbohydrate epitope that is required for selectin binding is the tetrasaccharide sialyl-Lewis$^x$ (SLe$^x$) or the related sialyl-Lewis$^a$ (SLe$^a$) [Varki, A., (1994), *PNAS*, 91, 7390–7397]. Agents which can interfere with selectin-ligand binding have potential use in the treatment of inflammatory conditions. A 96-well Scintillation Microtitre Plate, together with a radiolabelled synthetic SLe$^x$ glycoconjugate, was used to develop a cell free E-selectinligand binding assay which could be used to screen for selectin antagonists.

Materials and Methods

Coating Scintillation Microtitre Plates with Rabbit Immunoglobulin G

Rabbit immunoglobulin G (IgG) (Sigma Immunochemicals) was diluted to 20 μg/ml in phosphate buffered saline containing 2 mM $CaCl_2$, pH7.4, and 1 μg was added to the wells of an untreated 96-well scintillation microtitre plate (non-sterile, non-tissue culture treated). Negative control wells were coated with 50 μl of $PBS/CaCl_2$ buffer alone. The plate was incubated at 4° C. overnight, unbound rabbit IgG was removed and the plate was washed with 200 μl of $PBS/CaCl_2$ buffer three times.

Cell Adhesion Assay

An E-selectin fusion protein, containing the zz domain of protein A, was diluted to 4 μg/ml in $PBS/CaCl_2$ buffer and 200 ng was added to the wells of a rabbit IgG coated scintillation microtitre plate. To negative control wells 50 μl of $PBS/CaCl_2$ buffer was added. The plate was incubated at room temperature for 120 minutes after which time unbound E-selectin was removed and the plate was washed three times with 200μl of $PBS/CaCl_2$ buffer containing 0.1% bovine serum albumin (BSA). $^3$H-labelled $SLe^x$ glycoconjugate (Amersham) was added to wells ($5 \times 10^5$ scintillation counts in 50 μl of $PBS/CaCl_2/BSA$ buffer) and the plate was incubated at room temperature before counting on a Wallac Microbeta scintillation counter.

To demonstrate that the signal obtained was due to the specific interaction of the $^3H$-$SLe^x$ glycoconjugate ligand with the immobilized E-selectin fusion protein, the glycoconjugate ligand was added to wells in the presence of 5 mM EDTA or 500 μM 3'-sialyl-3-fucosyllactose (3'-S,3-FL). Monoclonal antibody (mAb) blocking experiments were also performed. To E-selectin coated wells, 1 μg of mouse anti-human E-selectin mAb (Chemicon, MAB2150), from a stock of 20 μg/ml in $PBS/CaCl_2$ buffer, was added and left to react for 60 minutes at room temperature. Control wells were incubated with 1 μg of an isotype matched anti-P-selectin mAb (Chemican, MAB2154). Unbound mAb was removed and the plate was washed three times with 200 μl of $PBS/CaCl_2/BSA$ buffer. $^3H$-$SLe^x$ glycoconjugate ligand was added and specific binding detected as described above.

Results

Figure 4:
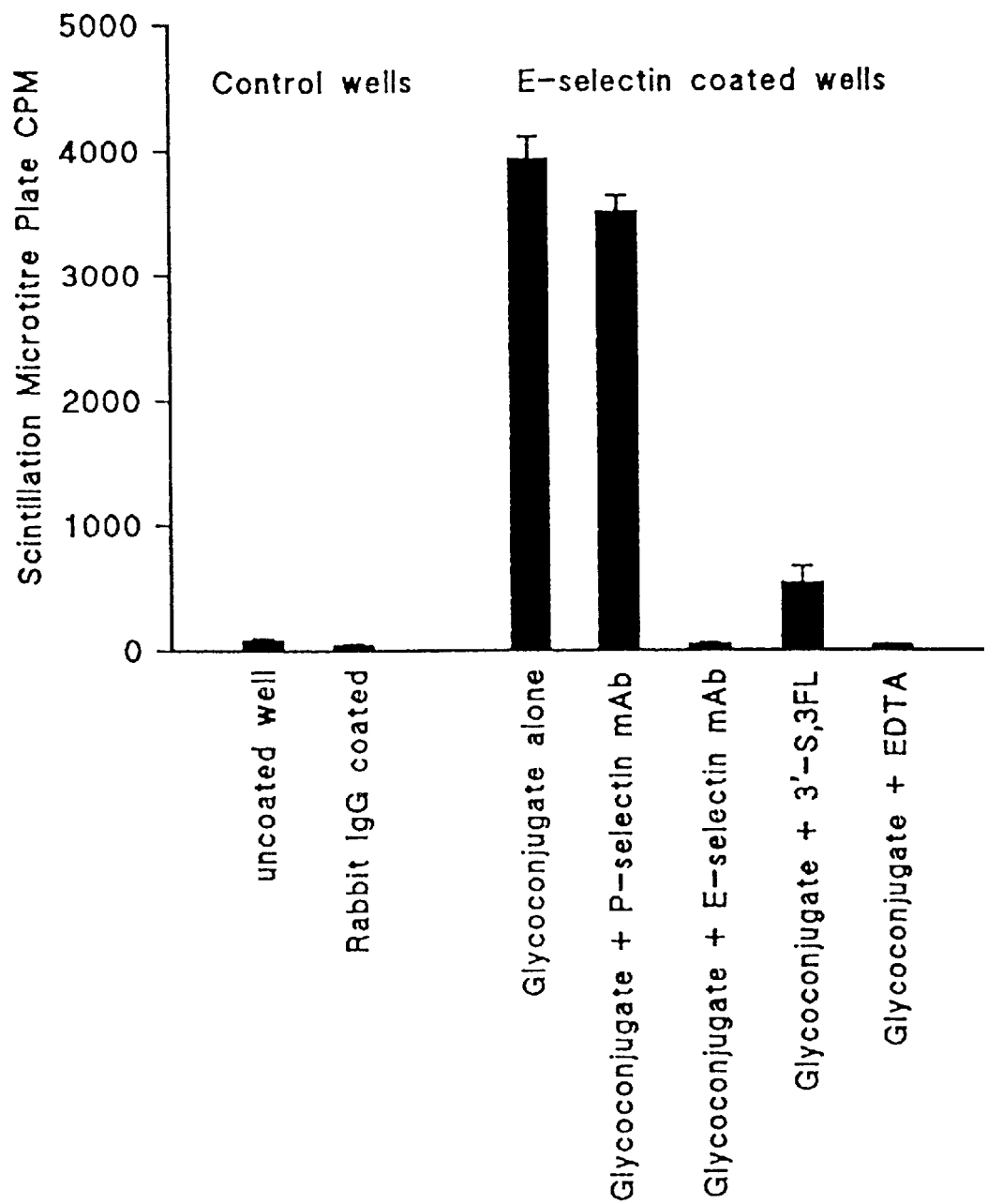

FIG. 4 shows binding of the $^3H$-$SLe^x$ glycoconjugate ligand to E-selectin coated onto the wells of a scintillation microtitre plate compared with binding to uncoated and rabbit IgG coated wells. The effects of an anti-E-selectin mAb, the soluble oligosaccharide 3'-S,3-FL and EDTA on glycoconjugate binding to E-selectin are also shown.

The results show that the $^3H$-$SLe^x$ glycoconjugate does not bind to uncoated or rabbit IgG coated wells. The low signal obtained represents non-specific interactions of the glycoconjugate with the plate surface. The signal obtained from binding of the $^3H$-$SLe^x$ glycoconjugate to E-selectin coated wells is over 80 times greater than non-specific signals. This signal is specific being completely inhibited by an anti-E-selectin mAb, but not an isotype matched control mAb, the oligosaccharide 3'-S,3-FL and by the calcium chelator EDTA.

Conclusions

The data in this example demonstrate the use of the scintillation microtitre plate to measure the specific adhesion of a radiolabelled ligand to E-selectin immobilized on the surface of a well. This cell free adhesion assay is sensitive to inhibition by mAb and soluble carbohydrate molecules and would be suitable for evaluation of inhibitors of selectin-mediated adhesion.

EXAMPLE 2

ASSAY OF REVERSE TRANSCRIPTASE UTILIZING STREPTAVIDIN COATED SCINTILLATING MICROTITRE PLATES

Introduction

Retroviruses such as the Human Immunodeficiency Virus (HIV) possess a reverse transcriptase (RT) that is required to produce proviral double stranded DNA copied from viral RNA and integrated into the host DNA. This absolute requirement of retroviruses for RT activity has made the enzyme a target for antiviral therapy, especially in the treatment of AIDS.

An assay for RT has been developed utilizing a streptavidin-derivatised scintillation microtitre plate and a protocol which does not require washing steps. This homogeneous assay uses a DNA/RNA polynucleotide system with biotin/streptavidin capture to generate a signal in the plate that is quantified by counting in a suitable microplate counter.

A 5'-biotinylated 16-mer oligo d(T) primer is annealed to a poly r (A) strand of approximately 300 bases in length to form a suitable template, which is bound, through biotin, to a streptavidin coated scintillation microtitre plate. Incorporation of thymidine 5'- triphosphate by reverse transcription results in chain extension from the 3'-end of the primer. If the dTTP is radiolabelled, the labeled duplex so formed will produce a specific signal because of its proximity to the scintillating base of the plate. Unincorporated labeled nucleotides are free in solution and are too distant from the base to produce a scintillation event in the plate base. The rate of increase in the signal is proportional to the activity of the enzyme used to initiate the reaction.

Materials and Methods

Preparation of scintillation microtitre plate

Both tissue culture treated (plasma discharge) and non-tissue culture treated plate wells were coated with a 100 μg/ml solution of streptavidin (Sigma, product No. S-8276) in phosphate buffered saline pH 7.4 (Gibco/BRL product No. 14190-201). Aliquots of 50 μl of this solution (sufficient to cover the base of the well only) were dried on to the well surface by incubation over 18 hours in a 37° C. incubator. Excess unbound streptavidin was subsequently removed by six washes using PBS Tween in an Amerlite™ plate washer.

Assay Procedure

Figure 5:
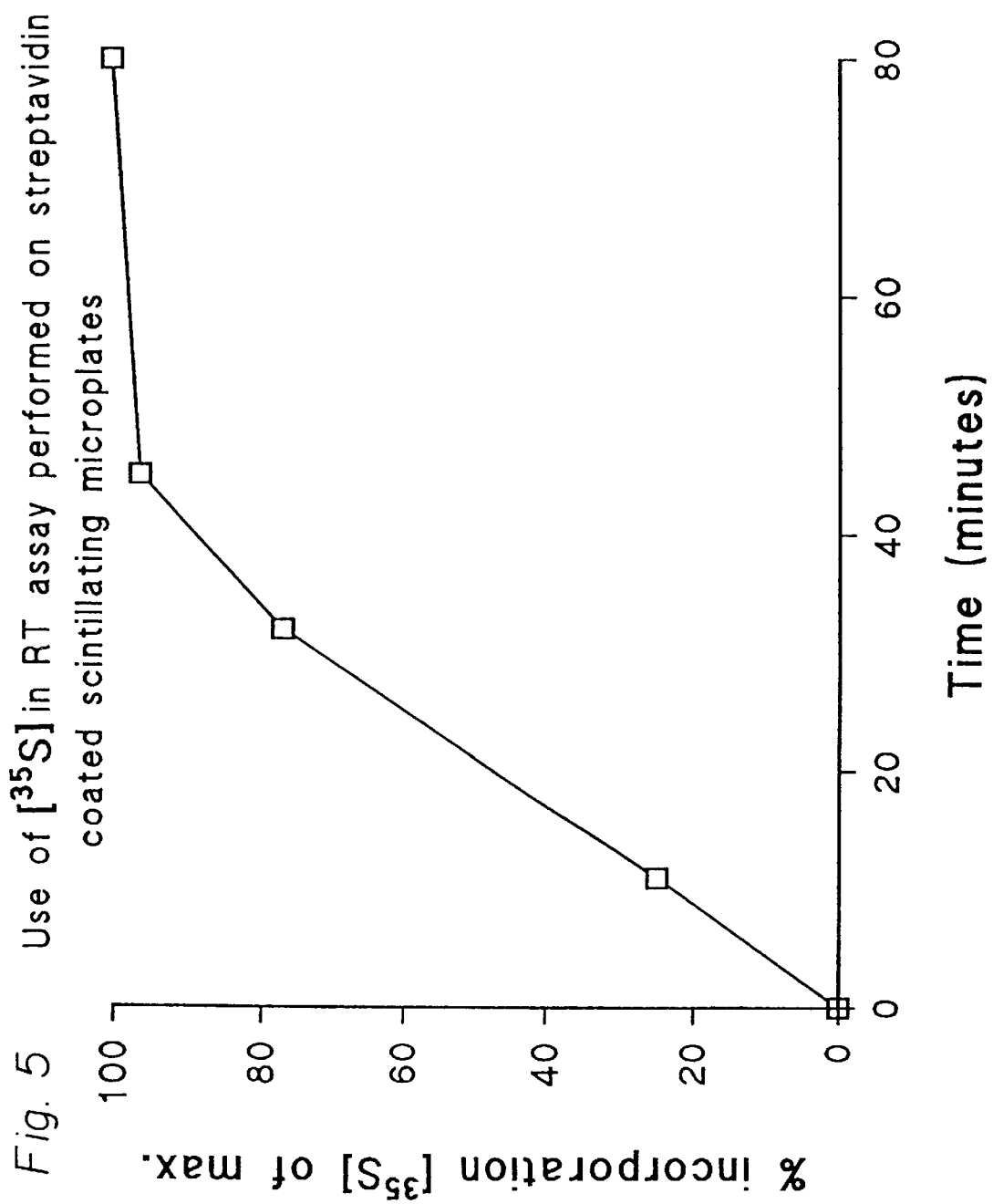
Figure 6:
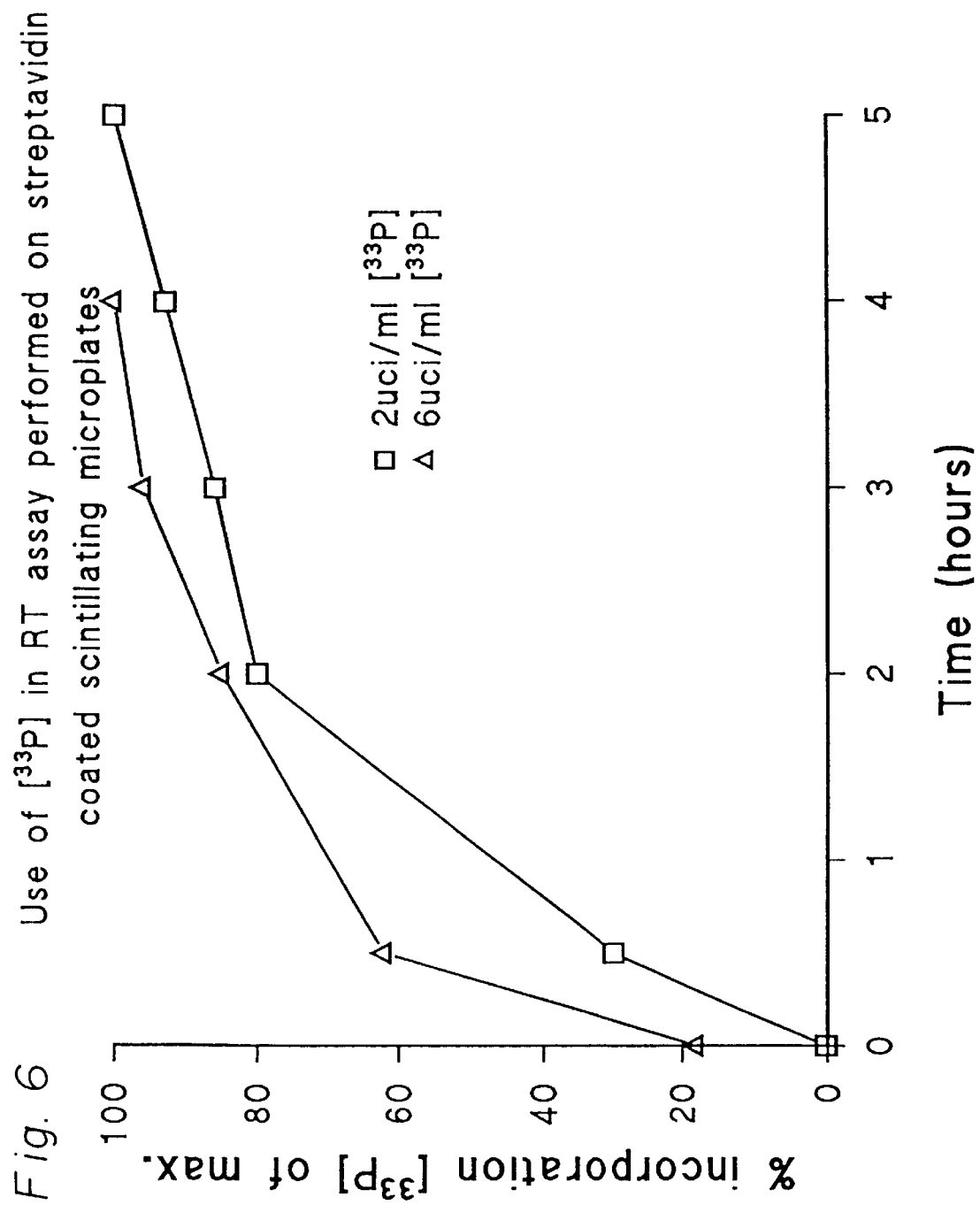

The biotinylated, ready annealed primer template was bound to the base of the streptavidin coated well and the excess removed. This was followed by [$^{35}$S]dCTPαS or [α$^{33}$P]dATP in 75 nM mixture of dATP, dCTP, dGTP and TTP buffered in 50 mM tris/HCl pH8.0, 80 mM KCl, 10 mM $MgCl_2$, 10 mM DTT and 0.05% w/v Nonidet P40. Two units of HIV-1 reverse transcriptase were added to initiate the reaction. Plates were incubated between readings at 37° C. Control, blank wells excluded enzyme. The progress of the incorporation of the radiolabel was monitored on a Micro-Beta counter using a normalized, crosstalk corrected program optimized for $^{35}$S or $^{33}$P. The time course for the incorporation is plotted in FIGS. 5 and 6. The time points are means of six determinations with blank values subtracted and expressed as a percentage of the maximum incorporation.

Results

At concentrations of 1 μi/ml [$^{35}$S] and both 2 μi/ml and 6 μci/ml [$^{33}$P] there is incorporation of radiolabel over time. See FIGS. 5 and 6.

Conclusion

The results demonstrate the use of a scintillating microtitre plate to monitor the transcriptase mediated incorporation of radiolabelled nucleotide with an oligonucleotide template. The homogeneous format renders the assay convenient since no washing steps are required and it can be completed within 4 hours. Furthermore the assay may be used to identify potential inhibitors or RT by means of their effect on the rate of production of nucleic and extension products.

EXAMPLE 3

[$^{125}$I] RADIOIMMUNOASSAY FOR ENDOTHELIN-1 USING ANTI-ENDOTHELIN-1 (15–21) RABBIT IgG COATED SCINTILLATION MICROTITRE PLATES.

Introduction

Endothelin-1 (ET-1) is one of three potent vasoconstrictor endothelin peptides (ET-1, ET-2 and ET-3) which are produced from larger precursor peptides by an endothelin converting enzyme in vascular endothelial cells (Bax, W. A. & Saxena, P. R., (1994) *TiPS* 15 379–386). ET-1 has 21 amino acid residues and two sets of disulphide bonds forming an intracellular loop structure within the peptide which is important for function (Yanagisawa, M. et al, (1988) *Nature* 322 411–415). In many mammalian species ET-1 produces a strong and sustained vasoconstrictive response in most arteries and veins (Yanagisawa, M. et al. (1988)). In addition to this vasoconstrictor activity, raised levels of the endothelins have been detected following myocardial infarction, pulmonary hypertension, migraine and other diseased states (Remuzzi, G. & Benigni, A., (1993) *Lancet* 342 589–593).

An $^{125}$I-based radioimmunoassay for the detection of ET-1, using 96 well Scintillation Microtitre plates coated with Rabbit IgG antibody raised against the C-terminal portion of ET-1, residues 15–21, has been developed.

Methods and Materials

Coating of Scintillation Microtitre Plates with Anti-ET-1 (15–21) Antibody

The anti-ET-1 (15–21) Rabbit IgG antibody (IBL) was diluted to 20 µg/ml with 50 mM carbonate/bicarbonate buffer pH9.6 (buffer capsules Sigma C-3041). 50 µl aliquots (1 µg antibody) were added to the wells of a 96 well, untreated Scintillation Micotitre plate (sterile, non-tissue culture treated). The plate lid was replaced and the plate was incubated at room temperature overnight (16 hours). Each well of the plate was then washed with 400 µl of 0.1% Tween 20, phosphate buffer pH7.5. After washing, the plate was blocked for 2 hours at room temperature by the addition of 100 µl 0.1% Germall II, Stabilcoat (BSI Corporation) to each well. This solution was removed and the plate inverted to dry at room temperature and then stored at 4 EC prior to the assay.

Assay Protocol

A 500 nM solution of ET-1 (Peninsula Labs. Inc.) was prepared in 0.1% BSA,PBS pH7.3 (assay buffer) for the non-specific binding (NSB) wells. From this stock solution a range of standard dilutions of ET-1 were prepared in assay buffer for the standard curve (1.22–625 fmols/well). 25 µl aliquots of the ET-1 standard solutions were added to appropriately designated wells on the anti-ET-1 (15–21) Rabbit IgG coated plate. 25 µl 50 nM ET-1 was added to NSB wells and 25 µl assay buffer was added to zero standard ($B_0$) wells. 25 µl of 0.5 µCi/ml (28000(cpm/well) (3-[$I^{125}$] Iodotyrosyl)ET-1 (Amersham;IM223) was then added to all wells on the plate. The total assay volume was 50 µl. The plate was incubated on a microtitre plate shaker overnight (16 hours), at 4° C. and then counted using a Wallac MicroBeta scintillation counter.

Results

Figure 7:
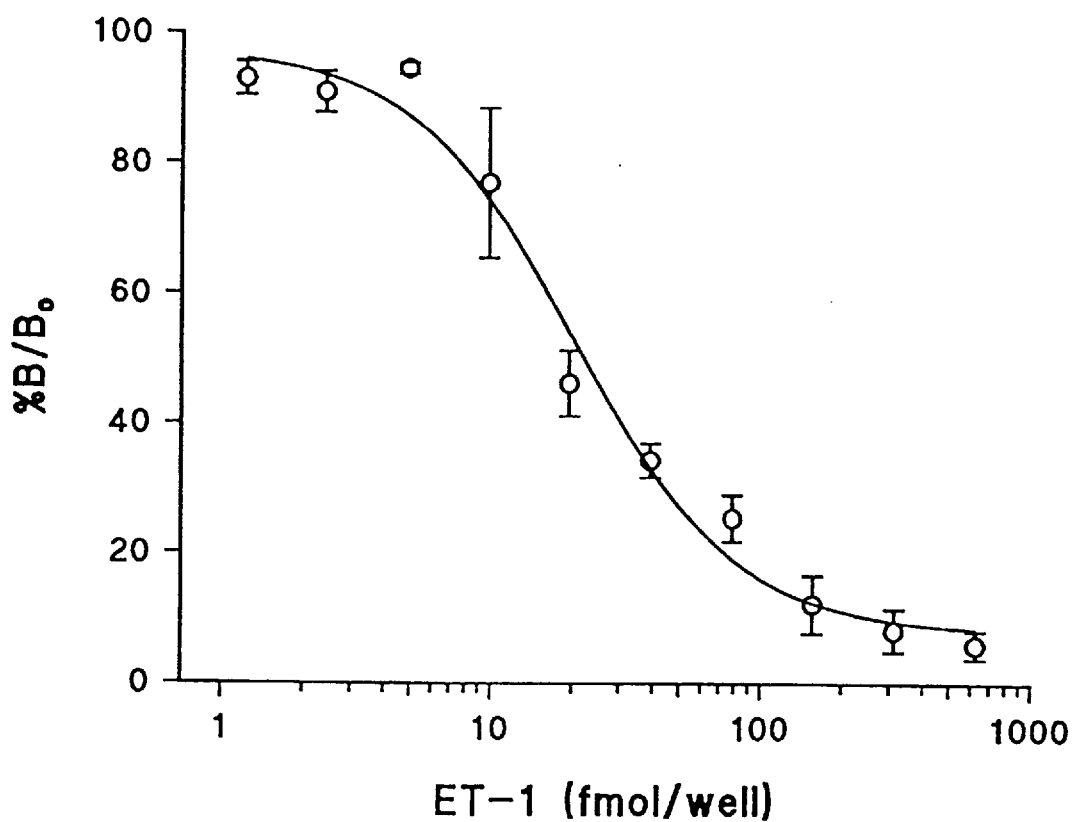

FIG. 7 shows the standard curve generated by plotting the % bound/$B_0$ versus ET-1 added in fmols/well. Results are the means (±s.e.m.) of at least three assay wells. Levels of ET-1 present in test samples can be read directly from the graph.

Conclusions

This example demonstrates that Scintillation Microtitre plates coated with specific purified monoclonal antibody can be used to perform radioimmunoassays for a particular peptide/protein present in test samples using the [$^{125}$I]-labeled peptide/protein as a tracer.

I claim:

1. A multiwell plate comprising an array of wells held in fixed relationship to one another, wherein each well is a vessel having an open top, side walls and a base, wherein the side walls are opaque and non-scintillant, and wherein the base includes a region and there is provided in or on an interior surface of the region a layer comprising a scintillant substance, said layer and/or said region being of a plastics material and which does not permit the attachment or growth of cells.

2. The multiwell plate of claim 1, wherein the base or each vessel is formed of a polymer containing phenyl or naphthyl moieties.

3. The multiwell plate of claim 1, comprising a body including side walls of individual wells, and a base plate composed of a polymer comprising the scintillant substance, the base plate sealed to the body so as to constitute closed bottom ends of individual wells.

4. The multiwell plate of claim 3, wherein the said base plate is silk screen printed with a grid array.

5. The multiwell plate of claim 1, comprising a body including side walls of individual wells, each individual well having a closed bottom end of a polymer comprising the scintillant substance.

6. The multiwell plate of claim 1, wherein the base is optically transparent.

7. A vessel having an open top, side walls and a base, wherein the side walls are opaque and non-scintillant, and wherein the base includes a region and there is provided in or on an interior surface of the region a layer comprising a scintillant substance, said layer and/or said region being of a plastics material and which does not permit the attachment or growth of cells.

8. The vessel of claim 7, wherein the base is formed of a polymer containing phenyl or naphthyl moieties.

9. The vessel of claim 7, wherein the base is optically transparent.

10. The vessel of claim 7, wherein the base is formed of a polymer containing a scintillant substance.

* * * * *